United States Patent [19]
Bussell

[11] Patent Number: 5,912,255
[45] Date of Patent: Jun. 15, 1999

[54] TOPICAL FLUOROQUINOLONE ANTIBIOTICS COMBINED WITH BENZOYL PEROXIDE

[76] Inventor: Letantia Bussell, 433 N. Camden Dr., Suite 805, Beverly Hills, Calif. 90210

[21] Appl. No.: 09/031,863

[22] Filed: Feb. 27, 1998

[51] Int. Cl.[6] .......... A61K 31/47; A61K 31/535; A61K 31/495; A61K 31/34
[52] U.S. Cl. .......... 514/311; 514/230.5; 514/252; 514/315; 514/468; 514/481; 514/859; 514/714
[58] Field of Search .......... 514/311, 315, 514/252, 230.5, 481, 468, 859, 714

[56] References Cited

U.S. PATENT DOCUMENTS

| | | | |
|---|---|---|---|
| 3,944,668 | 3/1976 | Cleaver | 424/227 |
| 4,038,388 | 7/1977 | Cleaver | 424/227 |
| 4,318,907 | 3/1982 | Kligman et al. | 514/164 |
| 4,355,028 | 10/1982 | Kligman et al. | 514/164 |
| 4,497,794 | 2/1985 | Klein et al. | 514/29 |
| 4,514,385 | 4/1985 | Damani et al. | 514/164 |
| 4,551,456 | 11/1985 | Katz | 514/254 |
| 4,692,329 | 9/1987 | Klein et al. | 514/29 |
| 5,374,432 | 12/1994 | Fox, Jr. et al. | 424/618 |
| 5,401,741 | 3/1995 | Sato et al. | 514/230 |
| 5,446,028 | 8/1995 | Klein et al. | 514/43 |
| 5,466,466 | 11/1995 | Muller | 424/78.37 |
| 5,476,854 | 12/1995 | Young | 514/24 |
| 5,648,389 | 7/1997 | Gans et al. | 514/557 |

OTHER PUBLICATIONS

Nishijima et al. J. Dermatol., 21(3), 166–71 (Abstract), 1994.

Vogt et al. Drugs, 49 (Suppl. 2), 266–8 (Abstract), 1995.

*Primary Examiner*—Kevin E. Weddington

[57] ABSTRACT

A pharmaceutical composition of all fluoroquinolones, including but not limited to, ciprofloxacin, ofloxacin, enoxacin, cinoxacin, pefloxacin, lomefloxacin, norfloxacin, tosufloxacin, fleroxacin, temafloxacin, trovafloxacin, and difloxacin, mixed with benzoyl peroxide in a vehicle for the topical treatment of a variety of skin conditions. The topical antibiotic and peeling agent will be in the form of a cream, ointment, lotion, gel, suspension, emulsion, cleansing bar, pledget, salve, tincture, spray, transdermal device, or other appropriate non-toxic pharmaceutical carrier.

5 Claims, No Drawings

TOPICAL FLUOROQUINOLONE ANTIBIOTICS COMBINED WITH BENZOYL PEROXIDE

BACKGROUND OF THE INVENTION

This invention relates to the topical application of all fluoroquinolones, including but not limited to, ciprofloxacin, ofloxacin, enoxacin, cinoxacin, pefloxacin, lomefloxacin, norfloxacin, tosufloxacin, fleroxacin, temafloxacin, trovafloxacin, and difloxacin, mixed with benzoyl peroxide in a vehicel for the treatment of a variety of organisms which infect the skin and a variety of inflammatory skin conditions. It will be used as a topical antibiotic and peeling agent, in the form of a cream, ointment, lotion, gel, suspension, emulsion, cleansing bar, pledget, salve, tincture, spray, transdermal device, or other appropriate non-toxic pharmaceutical carrier.

Fluoroquinolone antibiotics were first developed in the early 1960s but the earliest one, nalidixic acid, proved particularly susceptible to resistant bacteria thereby making it ineffectual over the long term. In the last five years, fluoroquinolones have become increasingly popular as chemical alterations have dramatically decreased the resistant bacteria appearing after treatment. This has made the family of fluoroquinolones more effective than a number of other antibiotics in combating bacterial infections. Fluoroquinolones attack bacteria by targeting DNA gyrase and by interfering with bacterial replication.

Theses antibiotics have been used extensively to treat respiratory tract infections, urinary tract infections, diarrhea, postoperative-wound infections, and many other conditions, because they are readily absorbed after oral and topical administration and exhibit potent in vitro activity against a broad spectrum of bacterial species. U.S. Pat. No. 5,476,854 describes the oral, intravenous and transdermal use of lomefloxacin to treat urinary tract infections, upper respiratory tract infections, sexually-transmitted infections, opthalmological infections and intestinal infections.

Fluoroquinolone antibiotics are active against a wide spectrum of gram-positive and gram-negative bacteria because of their broad antimicrobial activity. Varieties of fluoroquinolones, specifically ciprofloxacin, have been found to be effective against *Staphylococcus aureus, Streptococcus pneumoniae,* coagulese-negative *staphylococci, Streptococcus pyogenes, Staphylococcus epidermis, Pseudomonas aeruginosa, Escherichia coli, Klebsiella pneumoniae, Enterobacter cloacae, Proteus mirabilis, Proteus vulgaris, Providencia stuartii, Morganella morganii, Citrobacter diversus, Citrobacter freundii,* and other susceptible organisms. The mounting resistance of *Staphylococcus aureus* to both penicillin and erythromycin has made the fluoroquinolone antibiotics a viable alternative for the treatment of skin diseases. Studies of the effectiveness of the oral treatment of ciproflaxacin on skin and soft tissue infections have shown the medicine to have cure rates of 80% to 100%.

Topical compositions of fluoroquinolones and its derivatives have been used for opthalmic use, as seen in U.S. Pat. No. 4,551,456, which describes the use of norfloxacin and related antibiotics in the topical treatment of ocular infections. U.S. Pat. No. 5,374,432 describes a topical composition chosen from aminoglycoside antibiotics and quinolone antibiotics mixed in a sterile carrier, such as a water or ointment base, for the treatment of burns, other infection-prone wounds and ocular infection. U.S. Pat. No. 5,401,741 describes the topical treatment of ofloxacin mixed in an aqueous solution, for otopathy.

Combining a fluoroquinolone with a second active ingredient or antibiotic utilizes the two drugs' different mechanisms simultaneously to attack the many varieties of skin infections, inflammations and diseases. Fluoroquinolones have been tested in combination with coumermycin, amikacin, oxacillin, gentamicin, vanomycin, azlocillin, rifampin, and fosfomycin and have shown different degrees of synergy against *Staphylococcus aureus*. U.S. Pat. Nos. 3,944,668 and 4,038,388, combine tetracycline with 8-hydroxyquinoline in a topical or oral application as the two active ingredients behave synergistically against certain micro-organisms. U.S. Pat. No. 5,648,389 describes a topical composition mixing an antimicrobial, including ciprofloxacin, with a beta hydroxy acid and water soluble zinc compound to treat acne in humans.

At the same time, benzoyl peroxide has also proven effective against acne and other skin disorders. Benzoyl peroxide, formulated in 1905 and stabilized for effective use against acne in 1958, is an oxidizing agent which contains antibacterial and keratolytic properties. By decreasing the level of oil on the skin, benzoyl peroxide acts as a peeling agent. It attacks a number of gram-positive and gram-negative bacteria, particularly *Staphyloccocus epidermis*. Benzoyl peroxide has not been found to induce microbial resistance or severe side-effects so can be administered for a relatively long period. Benzoyl peroxide typically appears in cleansing bars, liquids, lotions, gels and creams in 2.5%, 5% and 10% concentrations.

Benzoyl peroxide has frequently been used in combination with other drugs to alleviate the symptoms of acne and skin disorders, particularly papulopustular and cystic acne. When mixed with an antibiotic such as erythromycin, benzoyl peroxide has been found to prevent the growth of antibiotic-resistant *staphylococci* which occurs when an antibiotic such as erythromycin is used alone. U.S. Pat. Nos. 4,497,794 and 4,692,329 use this combination of erythromycin and benzoyl peroxide for the treatment of acne. The presence of benzoyl peroxide allows the antibiotic to be more effective over the long term.

In addition, the irritation experienced with benzoyl peroxide has been lessened when placed in combination with clindamycin phosphate, an antibiotic. U.S. Pat. No. 5,466,446 discusses this effective combination. Combining benzoyl peroxide with sulphur in a lotion increases the amount of keratolysis to reduce facial oiliness and cause superficial peeling. In these cases, benzoyl peroxide provided dual help, by overcoming the problems inherent in the partnered drugs and by supplying a powerful antibacterial ingredient to the medication.

U.S. Pat. Nos. 4,318,907 and 4,355,028 describe the simultaneous and/or sequential use of salicylic acid and benzoyl peroxide to treat Acne Vulgaris. U.S. Pat. No. 4,514,385 describes mixing the two properties into a gel formula.

The bacteriologic profile and clinical course of uncomplicated soft tissue infections indicate that treatment with a fluoroquinolone antibiotic and benzoyl peroxide will result in resolution of the dermatological infection in most cases. Fluoroquinolone antibiotics are specifically effective against *Staphylococcus aureus, Streptococcus pneumoniae,* coagulese-negative *staphylococci, Streptococcus pyogenes, Staphylococcus epidermis, Pseudomonas aeruginosa, Escherichia coli, Klebsiella pneumoniae, Enterobacter cloacae, Proteus mirabilis, Proteus vulgaris, Providencia stuartii, Morganella morganii, Citrobacter diversus, Citrobacter freundii,* and other susceptible organisms which infect the skin. Benzoyl peroxide attacks *Staphyloccocus epidermis* and, against acne, acts secondarily as an antibacterial agent by oxidizing proteins, including the bacterial proteins in the sebaceous follicles. This chemical reaction has proven effective against non-inflamed lesions and mild papular acne, in particular. The individual pharmacological characteristics found separately in a fluoroquinolone antibiotic and benzoyl peroxide will work simultaneously to eliminate susceptible skin problems.

U.S. Pat. No. 5,409,917 describes the combination of a cephalosporin antibiotic with a carrier suitable for topical application such as an aqueous liquid, an alcohol vehicle, a water soluble gel, a lotion, an ointment, a nonaqueous liquid vehicle, a mineral oil vehicle, a blend of mineral oil and petrolatum, liposomes, a time-release patch, and a liquid-absorbed wipe. In addition, the patent includes the combination of a cephalosporin and benzoyl peroxide into a gel carrier.

Because fluoroquinolones have been proven effective against such a wide array of bacteria, topical treatment of a fluoroquinolone may accelerate the cure rate recorded by oral treatment by placing the antibiotic directly on the affected area. Mixing the antibiotic with benzoyl peroxide will provide an additional peeling agent, in a variety of effective mixtures, without diluting the effectiveness of the two active ingredients.

The objective of this invention is to combine all fluoroquinolones, including but not limited to, ciprofloxacin, ofloxacin, enoxacin, cinoxacin, pefloxacin, lomefloxacin, norfloxacin, tosufloxacin, fleroxacin, temafloxacin, trovafloxacin, and difloxacin, with benzoyl peroxide in a topical preparation as an antibiotic and peeling agent for the treatment of a variety of skin conditions. The composition will be in the form of a cream, ointment, lotion, gel, suspension, emulsion, cleansing bar, pledget, salve, tincture, spray, transdermal device, or other appropriate non-toxic pharmaceutical carrier.

OTHER REFERENCES CITED

Brody, Terri., and Myles L. Pensak, "The Fluoroquinolones," *The American Journal of Otology*, vol. 12, no. 6, pp. 477–479, November 1991.

Brogden, R. N., and G. S. Avery, "Benzoyl Peroxide Acne Lotions: An Independent Report," *Drugs*, vol. 6, pp. 417–421, 1974.

Burke, B., E. A. Eady, and W. J. Cunliffe, "Benzoyl Peroxide Versus Topical Erythromycin in the Treatment of Acne Vulgaris," *British Journal of Dermatology*, vol. 108, pp. 199–204, 1983.

Douidar, Samir M., and Wayne R. Snodgrass, "Potential Role of Fluoroquinolones in Pediatric Infections," *Reviews of Infectious Diseases*, vol. 11, no. 6, pp. 878–889, November–December 1989.

Eady, E. A., R. A. Bojar, C. E. Jones, J. H. Cove, K. T. Holland, and W. J. Cunliffe, "The Effects of Acne Treatment with a Combination of Benzoyl Peroxide and Erythromycin on Skin Carriage of Erythromicin-resistant Propionbacteria," *British Journal of Dermatology*, vol. 134, pp. 107–113, 1996.

Fong, I. W., "The Role of Fluoroquinolones in the Management of Skin, Soft Tissue, and Bone Infections," *Clinical and Investigative Medicine*, vol. 12, no. 1, pp. 44–49, 1989.

Gordon, B., "Neglected Aspects in the Management of Acne," *Journal of the Royal Society of Medicine Supplement*, vol. 78, no. 10, pp. 10–14, 1985.

Guay, David R., "The Role of Fluoroquinolones," *Pharmacotherapy*, supplement to vol. 12, no. 6, pp. 71S–85S, 1992.

Hurwitz, S., "Acne Vulgaris: Pathogensis and Management," *Pediatrics in Review*, vol. 15, no. 3, pp. 47–52, March 1994.

Ives, Timothy J., "Benzoyl Peroxide," *American Pharmacy*, vol. NS32, no. 8, pp. 33–38, August 1992.

Kligman, Albert M., "Acne Vulgaris: Tricks and Treatments. Part II: The Benzoyl Peroxide Saga," *Cutis*, vol. 56, pp. 260–261, November 1995.

Neu, Harold C., "Use of Fluoroquinolone Antimicrobial Agents by Cardiovascular and Cardiopulmonary Surgeons," *Texas Heart Institute Journal*, vol. 17, no. 1, pp. 12–21, 1990.

Neu, Harold C., "Synergy of Fluoroquinolones with Other Antimicrobial Agents," *Reviews of Infectious Diseases*, vol. 11, suppl. 5, pp. S1025–S1035, July–August 1989.

Nolen, Thomas M., "Clinical Trials of Cefprozil for Treatment of Skin and Skin-Structure Infections: Review," *Clinical Infectious Diseases*, vol. 14(Suppl 2), pp. S255–263, 1992.

Powers, Robert D., Robert Schwartz, Rodney M. Snow, and Dabney R. Yarbrough III, "Ofloxacin versus Cephalaxin in the Treatment of Skin, Skin Structure, and Soft-Tissue Infections in Adults," *Clinical Therapeutics*, vol. 13, no. 6, pp. 727–736, 1991.

Rodriguez, William J., and Bernhard L. Wiedermann, "The Role of Newer Oral Cephalosporins, Fluoroquinolones, and Macrolides in the Treatment of Pediatric Infections," *Advances in Pediatric Infectious Diseases*, vol. 9, pp. 125–159, 1994.

Talley, Joseph H., "Fluoroquinolones: New Miracle Drugs?" *Postgraduate Medicine*, vol. 89, no. 1, pp. 101–103, 106–108, 111–113, January 1991.

Tucker, S. B., R. Tausend, R. Cochran, and S. A. Flannigan, "Comparison of Topical clindamycin Phosphate, Benzoyl Peroxide, and a Combination of the Two for the Treatment of Acne Vulgaris," *British Journal of Dermatology* vol. 110, pp. 487–492, 1984.

DESCRIPTION OF THE INVENTION

While the invention will be described in connection with a preferred embodiment and method, it will be understood that I do not intend to limit the invention to the embodiment or method. On the contrary, I intend to cover all alternatives, modifications, and equivalents as may be included within the spirit and scope of the invention as defined by the appended claims.

In accordance with the present invention, the selected fluoroquinolone antibiotic in combination with benzoyl peroxide in the form of an ointment, lotion, cream, gel, suspension, emulsion, cleansing bar, pledget, salve, tincture, spray, transdermal device, or other appropriate non-toxic pharmaceutical carrier. As stated above, the resulting composition is used for the topical treatment of a variety of skin infections conditions.

Compositions are prepared by mixing a selected fluoroquinolone antibiotic as an active ingredient with benzoyl peroxide (in representative percentages by weight of 2.5%, 5.0%, 10.0%, or 2.0% as examples but may range from 01.% to 9.0%). In this solution, a fluoroquinolone antibiotic will be added to an independent mixture of benzoyl peroxide, whereby the fluoroquinolone retains its medicinal properties and allows for the topical administration of the antibiotic.

In the following compositions, "Active Ingredient," means any selected fluoroquinolone antibiotic. The respective concentrations of any of the ingredients can vary (0.1% to 99.0%, for example) as different strengths of the composition are produced. The inactive ingredients are representative only and may vary according to need. Various preservatives (such as benzoic acid) will also be added as needed. These preparations describe the manner and processing of using this invention and are to be construed as exemplary embodiments of the inventive concept and not as limitations thereof.

|  | mg/g |
|---|---|
| Example 1 Ointment | |
| Active Ingredient | 10.0 |
| Benzoyl Peroxide | 50.0 |
| SD Alcohol 40 | 360.0 |
| Mineral Oil | 50.0 |
| White Petroleum q.s. ad | 1.0 |
| Example 2 Lotion | |
| Active Ingredient | 10.0 |
| Benzoyl Peroxide | 50.0 |
| SD Alcohol 40 | 360.0 |
| Polyethylene glycol 400 | 100.0 |
| Hydroxypropyl cellulose | 5.0 |
| Propylene glycol q.s. ad | 1.0 |
| Purified Water q.s. ad | 100.0 |
| Example 3 Cream | |
| Active Ingredient | 10.0 |
| Benzoyl Peroxide | 50.0 |
| SD Alcohol 40 | 360.0 |
| Isopropyl myristate | 100.0 |
| Polyoxyethylene (2) monostearyl ether | 10.0 |
| Polyoxyethylene (20) monostearyl ether | 25.0 |
| Propylene glycol | 100.0 |
| Purified water q.s. ad | 1.0g |
| Example 4 Gel | |
| Active Ingredient | 10.0 |
| Benzoyl Peroxide | 50.0 |
| SD Alcohol 40 | 360.0 |
| Hydroxypropyl cellulose | 50.0 |
| Allantoin | 10.0 |
| Propylene glycol | 50.0 |

-continued

|  | mg/g |
|---|---|
| Purified water q.s. ad | 1.0g |
| Example 5 Suspension | |
| Active Ingredient | 10.0 |
| Benzoyl Peroxide | 50.0 |
| SD Alcohol 40 | 360.0 |
| Polyethylene glycol 400 | 100.0 |
| Hydroxypropyl cellulose | 5.0 |
| Purified glycol q.s. ad | 1.0g |
| Example 6 Emulsion | |
| Active Ingredient | 10.0 |
| Benzoyl Peroxide | 50.0 |
| SD Alcohol 40 | 360.0 |
| Polyethylene glycol 400 | 100.0 |
| Hydroxypropyl cellulose | 5.0 |
| Purified glycol q.s. ad | 1.0g |

I claim:

1. A method of topically treating acne and other skin diseases which comprises administering to an individual a composition of a fluoroquinolone antibiotic present in a vehicle containing benzoyl peroxide, applied directly to the affected areas of the human skin.

2. A method described in claim 1 wherein the fluoroquinolone antibiotic is selected from a group consisting of, but is not limited to, ciprofloxacin, ofloxacin, enoxacin, cinoxacin, pefloxacin, lomefloxacin, norfloxacin, tosufloxacin, fleroxacin, temafloxacin, trovafloxacin, and difloxacin, in the form of an ointment, cream, lotion, liquid, gel, suspension, emulsion, cleansing bar, pledget, salve, tincture, spray, transdermal device or other appropriate non-toxic pharmaceutical vehicle.

3. The method described in claim 1 wherein the fluoroquinolone antibiotic is present in a range from about 5% to about 10% by weight of the composition.

4. The method described in claim 1 wherein the benzoyl peroxide is present in a weight percent from 2% to about 10% by weight of the composition.

5. A method described in claim 1 wherein the topical carrier is present in a weight percent from 75.0% to 94.9%.

* * * * *